United States Patent [19]

Zare et al.

[11] Patent Number: 5,298,134

[45] Date of Patent: Mar. 29, 1994

[54] CAPILLARY DEVICE

[75] Inventors: Richard N. Zare, Stanford; Xiaohua Huang, Mountain View; Stephen L. Pentoney, Jr., Yorba Linda, all of Calif.

[73] Assignee: Board of Trustees of the Leland Stanford Junior University, Palo Alto, Calif.

[21] Appl. No.: 64,849

[22] Filed: May 20, 1993

Related U.S. Application Data

[60] Continuation of Ser. No. 902,915, Jun. 23, 1992, abandoned, which is a division of Ser. No. 235,953, Aug. 24, 1988, abandoned.

[51] Int. Cl.$^5$ .................... G01N 27/26; G01N 27/447
[52] U.S. Cl. .............................. 204/180.1; 204/299 R
[58] Field of Search .................... 204/299 R, 180.1

[56] References Cited

U.S. PATENT DOCUMENTS

| | | | |
|---|---|---|---|
| 3,933,430 | 1/1976 | Hare | 73/61.52 X |
| 4,028,056 | 6/1977 | Snyder et al. | 73/61.52 X |
| 4,165,219 | 8/1979 | Huber | 73/61.52 X |
| 4,394,263 | 7/1983 | Dosch et al. | 210/198.2 |
| 4,529,230 | 7/1985 | Fatula, Jr. | 285/341 |
| 4,675,300 | 7/1987 | Zare et al. | 436/172 |
| 4,680,201 | 7/1987 | Hjerten | 427/230 |
| 4,696,904 | 9/1987 | Stevens et al. | 73/61.52 X |
| 4,936,974 | 6/1990 | Rose et al. | 204/299 R |
| 4,994,165 | 2/1991 | Lee et al. | 204/180.1 X |
| 5,110,431 | 5/1992 | Moring | 204/180.1 |
| 5,180,479 | 1/1993 | Rose | 204/299 R |

FOREIGN PATENT DOCUMENTS

| | | |
|---|---|---|
| 53-29193 | 3/1978 | Japan . |
| 58-148951 | 5/1983 | Japan . |
| 60-138450 | 7/1985 | Japan . |
| 60-140151 | 7/1985 | Japan . |

OTHER PUBLICATIONS

"On-Line Connector for Microcolumns: Application to the On-Column . . . ," by Pentoney, Jr. et al., *Anal. Chem.*, 60:2625-2626, Dec. 1988.

Patent Abstracts of Japan, vol. 9, No. 105, May 9, 1985.
"A Simple High Temperature, High Presure Safe T-piece . . . ," by Reider et al., vol. 9, No. 10, Oct. 1986, Heidelberg, Del.
"Microbore High-Performance . . . of Dns-Amino Acids", Miyaguchi et al., Journal of Chromatography, 316 (1984) 501-505.
"Amperometric Detection of . . . Post-Column Reaction", Watanabe, Journal of Chromatography, 316 (1984) 495-500.
"Fundamentals of Reaction Detection Systems", Lillig and Engelhardt, Reaction Detection in Liquid Chromatography, pp. 1-15.
"Preparative Capillary Isotachophoresis, Principle and Some Applications" Journal of Chromatography, 119 (1976) 9-24.
"Fundamentals of Reaction Detection Systems," Lillig and Engelhart, Reaction Detection in Liquid Chromatography, pp. 1-15.
"Post-Capillary Fluorescence Detection in Capillary Zone Electrophoresis Using o-Phthaldialdehyde," by ROse, Jr. et al., *Journ. of Chromatog.*, 447 (1988) 117-131.
"Laser-Induced Fluorescence Detection in Capillary Zone Electrophoresis," by Nickerson et al., Chemistry Department, Chapel Hill, N.C.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

A cross or T-shaped device is disclosed for use in capillary electrophoresis or capillary chromatography. The device includes a first capillary tube and a second capillary tube connected to the first tube at a point between the two ends of the first tube so that the contents flowing in the second tube will mix with a fluid flowing in the first tube. The two tubes enclose spaces with cross-sectional dimensions less than about 200 microns. The two tubes are connected so that there is substantially no dead space at the connection. The device is made by boring a hole at a selected location in the first tube, introducing an elongated guide member into the hole, threading the member into the second tube until the second tube contacts the first tube. The second tube is then permanently connected to the first tube and the guide member is then removed to form a T-shaped device. To form the cross-shaped device, a second hole is drilled at a location opposite to the first hole and a guide member is introduced into the second hole as well. A third tube is threaded onto the guide member on the opposite side of the second tube until it contacts the first tube. The third tube is also permanently connected to the first tube and the guide member is removed to yield a device with a cross-shaped configuration.

9 Claims, 3 Drawing Sheets

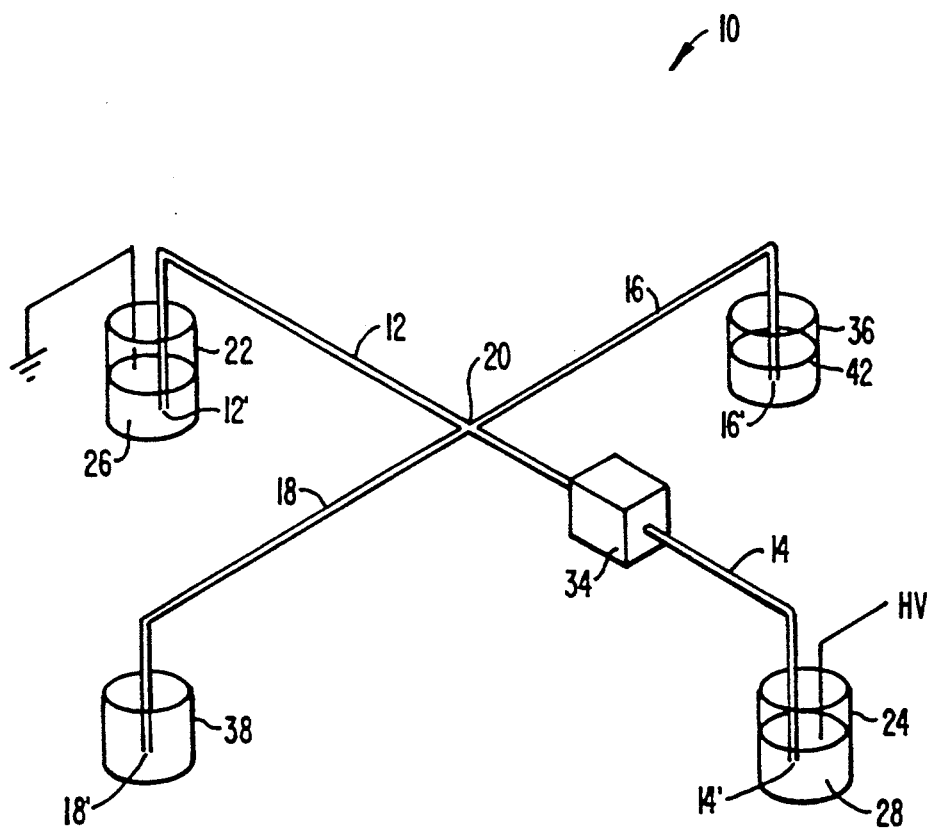
FIG._1.

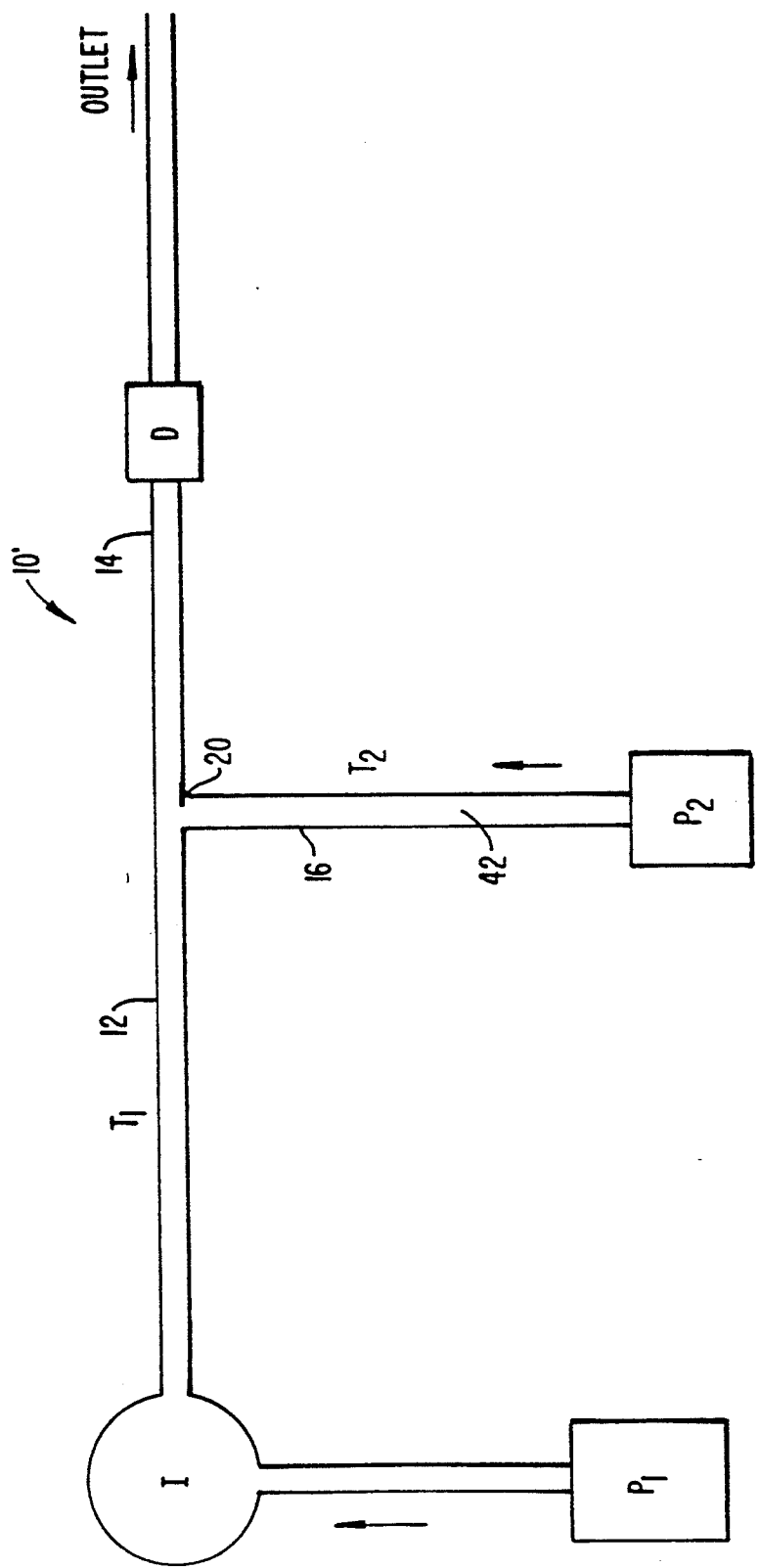
FIG._2.

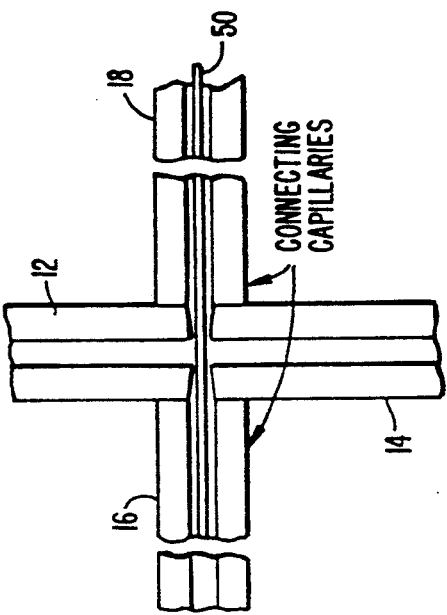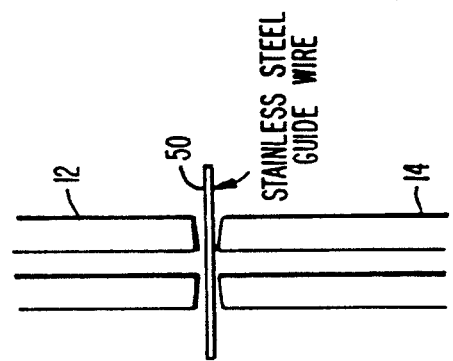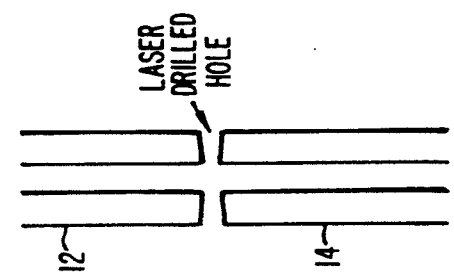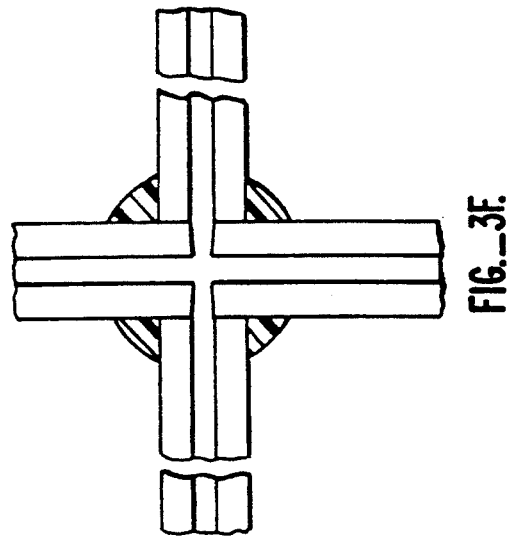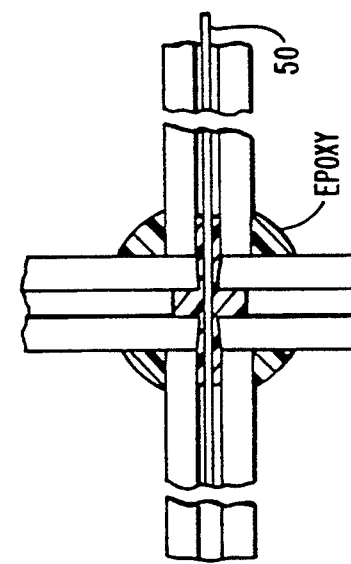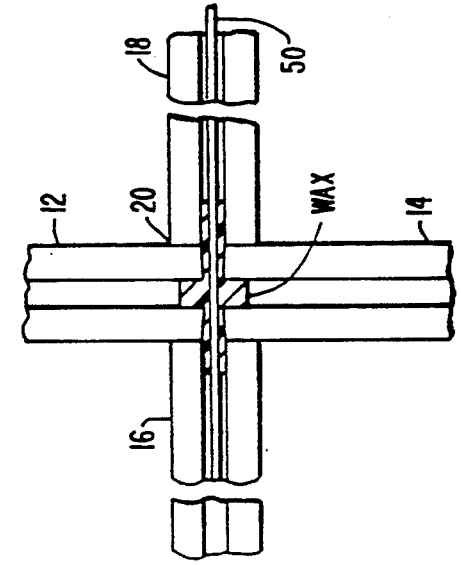

CAPILLARY DEVICE

REFERENCE TO RELATED APPLICATION

This is a continuation patent application of divisional patent application Ser. No. 902,915, filed Jun. 23, 1992, now abandoned whose parent application is patent application Ser. No. 235,953, filed Aug. 24, 1988 now abandoned.

BACKGROUND OF THE INVENTION

This invention relates in general to capillary devices and in particular to a capillary device useful in capillary electrophoresis and capillary chromatography.

Capillary zone electrophoresis (CZE) in small capillaries has proven useful as an efficient method for the separation of solutes. An electric field is applied between the two ends of a capillary tube into which an electrolyte containing the solutes is introduced. The electric field causes the electrolyte to flow through the tube. Some solutes will have higher electrokinetic mobilities than other solutes so that the solutes form zones in the capillary tube during the flow of the electrolytes through the capillary. To aid the analysis of the contents of the electrolyte or to aid the detection of such contents, fluids have been introduced in a second capillary connected to the main capillary through which the electrolyte flows. This causes the fluid introduced in the second capillary to mix with portions of the electrolyte in the main capillary to aid the analysis, detection or separation in the CZE process.

In order to introduce another fluid into the electrolyte in the main capillary, the main capillary has to be connected at a location between its two ends to a second capillary tube. One type of connection is formed by breaking the main capillary into two parts and connecting the two parts to a third tube through a T-shaped connector. This and other types of connectors for introducing another fluid to mix with the electrolyte are disadvantageous because they contain too much dead space at the connection between the two capillaries.

It is frequently desirable to detect compounds in the electrolyte occurring in very small quantities. For this reason, the CZE process is performed with very small capillaries to enhance the separation of such trace compounds from other constituents of the electrolyte. Such traces will be detected when certain peaks occur in electropherograms. When such trace compounds pass through the connection, the dead space at such connection will cause the trace compounds to be mixed with other constituents in the electrolyte; this has the effect of broadening the peaks in the electropherograms. This reduces the sensitivity of detection and resolution of traces of compounds and is therefore undesirable. It is therefore desirable to provide devices which permit a fluid to be introduced into the electrolyte during its flow in a CZE process in which the peak broadening effects are reduced.

In capillary chromatography, analysis and separation are achieved in a manner similar to the CZE process except that the fluid in the capillary is moved by pressure instead of by an electric field. For considerations similar to those described above, it is desirable to provide a capillary device which permits a second fluid to be introduced at any point in the flow of a first fluid through a main capillary in capillary chromatography where peak broadening effects are reduced.

SUMMARY OF THE INVENTION

The device of this invention is for use in capillary electrophoresis or capillary chromatography. The device comprises a first capillary tube enclosing a first space with cross-sectional dimensions less than about 200 microns and a second capillary tube enclosing a second space with cross-sectional dimensions less than about 200 microns. The second tube is connected to the first tube at a point between the two ends of the first tube so that when a first fluid is flowing in the first tube, a second fluid flowing in the second tube will mix with the fluid in the first tube, wherein the two tubes are connected so that there is substantially no dead space at the connection.

The device is made by boring a hole at a selected location into the first tube, where the location is between the two ends of the first tube, introducing an elongated guide member into the hole, threading the member into the second tube until the second tube is in contact with the first tube. The second tube is then permanently connected to the first tube and the guide member is then removed. A T-shaped device is the result. In the preferred embodiment, a second hole is drilled into the first tube at a location substantially opposite to the first hole and the guide member is introduced through the second hole as well. A third tube is moved relative to the member and the first tube so that the member is threaded into the third tube and the third tube contacts the first tube and forms a cross-shape configuration with the first and second tubes. The third tube is also permanently connected to the first tube and the guide member is removed from the third tube as well so that a cross-shaped configuration formed by the first, second and third tubes result.

BRIEF DESCRIPTION OF THE DRAWINGS

FIG. 1 is a schematic view of a capillary electrophoretic system to illustrate the invention.

FIG. 2 is a schematic view of a capillary chromatographic system to illustrate the invention.

FIGS. 3A–3F are cross-sectional views of portions of capillary tubes and other elements for connecting two or three capillary tubes to illustrate the preferred embodiment of the invention.

DETAILED DESCRIPTION OF THE INVENTION

FIG. 1 is a schematic view of an electrophoretic system for performing CZE processes employing device 10 to illustrate the preferred embodiment of the invention. As shown in FIG. 1; device 10 comprises a main capillary tube which includes two portions 12, 14, and a second capillary tube comprising two portions 16, 18 where the two tubes are connected at connection 20 in a manner so that a second fluid flowing in the second tube will mix with a first fluid flowing in the main capillary tube. The two ends 12', 14' of the main capillary tube are in containers 22, 24 which may be beakers. Containers 22, 24 contain electrolytes 26, 28 respectively. An electrical potential is applied between the two electrolytes as shown in FIG. 1, causing the electrolyte 26 to flow through portion 12 and then portion 14 of the main capillary to container 24. During its flow, the constituents of the electrolyte 26 are detected by detector 34.

To aid the separation and analysis in the CZE process, a second fluid is introduced and mixed with the electrolyte 26 during its flow through portion 14 by means of the second capillary tube. The ends 16', 18' of the second capillary are placed in containers 36, 38 respectively. A liquid 42 is placed in container 36 and container 36 is placed at a higher elevation than container 38. After liquid 42 is introduced in the portion 16, it will flow towards connection 20 to portion 18 and is subsequently discharged into container 38. Since the space enclosed by the second capillary are connected to the space enclosed by the main capillary at connection 20, a small portion of the liquid 42 will become mixed with the portion of the electrolyte in the main capillary and the mixture will flow through portion 14. Thus separation can be enhanced and such separation can be detected by detector 34.

Device 10 differs from existing devices in that both the first and second capillary tubes enclose spaces whose cross-sectional dimensions are less than 200 microns, and in that the two capillaries are connected so that the spaces enclosed therein are also connected with substantially no dead space at the connection. This reduces or eliminates the peak broadening effect of existing capillary devices. Preferably both the main and secondary capillary tubes enclose spaces whose cross-sectional dimensions are substantially between 5 and 200 microns.

The above described device is useful in capillary chromatography (GC or LC) or in CZE processes. Thus, device 10 is useful:

1. To provide on-column derivatization of the contents of the main capillary to aid analysis/separation;

2. To introduce a change in the contents of the main capillary, such as a pH change, or a salt ion concentration change, to aid separation/analysis;

3. To place a reference electrode in intimate contact with the contents of the main capillary for electrochemical detection purposes;

4. To introduce scintillation fluid into the main capillary by means of the second capillary to aid radioactive decay detection; and 5. To permit selective removal of the contents of the first capillary in the vicinity of the connection 20.

While in the preferred embodiment, device 10 is cross-shaped, device 10 can also be a T-shaped device instead. In such configuration, device 10 will simply comprise the main capillary having portions 12, 14 and the secondary capillary having only portion 16. When such a device is used in CZE processes, as described above in reference to FIG. 1, liquid 42 introduced into the second capillary 16 will flow entirely into portion 14 of the main capillary. For some applications, the cross-shaped configuration of device 10 is advantageous over the T-shaped configuration since only a small portion of the liquid 42 introduced into the second capillary will be introduced into portion 14 of the main capillary. In either the cross-shaped or the T-shaped configurations, there is substantially no dead volume at connection 20 so that peak broadening is reduced.

FIG. 2 is a schematic view of a capillary chromatographic system to illustrate the invention. As shown in FIG. 2, the device 10' is of the type described above having a T-shaped configuration. Identical parts in FIGS. 1, 2 are labeled by the same numerals. As shown in FIG. 2, instead of using an electrical means, the fluid in portions 12, 14 of the main capillary as well as liquid 42 in the second capillary 16 are moved by pressure generating devices such as pumps P1, P2 instead of electrical means as in FIG. 1. Since device 10' is such that there is substantially no dead space or volume at connection 20, band broadening is reduced.

Another aspect of the invention is directed towards a method for making devices 10, 10' of FIGS. 1 and 2. FIGS. 3A–3F are partial cross-sectional views of portions 12, 14, 16, 18 of FIG. 1 as well as other elements used for connecting the two capillary tubes to illustrate a preferred method for making device 10 of FIG. 1. First a hole is drilled in opposing walls of the main capillary as shown in FIG. 3A; the holes in the opposing walls are located so that they are substantially opposite to each other. The two capillaries are preferably composed of an insulating material such as fused quartz although other insulating materials such as Teflon, glass or ceramic may also be used. The holes may be drilled by means of a carbon dioxide laser using an X-Y translation stage and a microscope, although other lasers and instruments may also be used instead. The main capillary is preferably 5–200 microns in inside diameter. The holes drilled are preferably 5–50 microns in diameter. A guide member 50 which is of a dimension which fits snuggly inside the holes serves to guide the connection of the second capillary to the main capillary as described below. A metal wire which is of sufficient stiffness may be used as the guide member.

FIG. 3B shows the configuration after the guide member has been inserted into the holes. Portions 16, 18 of a second capillary tube are then moved relative to the guide member and portions 12, 14 until the two portions are threaded onto the guide wire and until they contact portions 12, 14 as shown in FIG. 3C. A masking agent is then introduced to mask the member; such masking agent may be wax or liquified polyethylene glycol. The masking agent can be introduced simply by depositing a small quantity of the agent at connection 20 and slightly warming the agent to melt it so that the agent defuses into the space between the wire and the inner surfaces of the two capillary tubes as shown in FIG. 3D. Excess masking agent remaining on the outside surfaces of portions 12–18 may be removed. The result is shown in FIG. 3D. Portions 12, 14, 16, 18 are then permanently connected or attached. This can be accomplished with epoxy resin or other chemically inert adhesives. This is shown in FIG. 3E. After curing, wire 50 is removed by heating slightly the connection 20. Since the guide member is prevented from being permanently attached to the two capillary tubes by the masking agent, a slight heating of connection 20 will melt the agent to facilitate the withdrawal of the guide member.

From the above-description, it will be evident that there is substantially no dead space or volume at connection 20.

If a T-shaped device such as device 10' of FIG. 2 is desired, the above described procedure needs to be modified only as follows. A hole is drilled in only one side wall of the main capillary and the guide wire is introduced into such single hole. Only one tube such as tube 16 is threaded onto the wire. The masking agent is introduced in the same manner as described above and the three tubes are glued together by epoxy and the guide member withdrawn in the same manner described above.

While the above-described method has been found to be satisfactory, a device with better qualities is formed by connecting the two capillary tubes not by adhesives such as an epoxy resin but by heating connection 20 until the material of the two capillaries such as quartz or glass melts at the connection so that the portions 12, 14, 16, 18 are permanently connected when the melted quartz or glass is cooled. Thus in the preferred embodiment, the two capillary tubes are connected without any adhesives. Since no adhesives are used in the preferred embodiment, the guiding member will not become attached to the tubes so that no masking agent will be required. This has the advantage of simplifying the process for making the device. Thus in the preferred method, the steps of applying a masking agent and applying adhesives and of warming the connection in order to remove the guide member are omitted.

The above description of the details of implementation, method and composition are merely illustrative of the invention. Different variations may be within the scope of the invention which is to be limited only by the appended claims.

What is claimed is:

1. A method for separation in a capillary comprising:
   providing a sample to the capillary;
   providing to the capillary at a location along the capillary a reagent that will react chemically in the capillary with the sample to aid the detection or separation of the sample, said sample having components, thereby rendering at least a component of the sample detectable or enhancing the separation of the sample;
   applying an electrical potential across the capillary, causing the sample to migrate through the capillary and to separate in the capillary into its components; and
   detecting at a second location along the capillary downstream from said first location at least one of said components of the sample.

2. The method of claim 1, said capillary having an inlet end and another end, wherein said reagent providing step provides said reagent to the capillary at said first location between the inlet and the other end of the capillary.

3. The method of claim 1, said capillary having a side tube connected to it at said first location so that when a sample is moving in the capillary, a reagent moving in the side tube will mix with the sample in the capillary, wherein said reagent providing step provides the reagent through said side tube to the capillary.

4. The method of claim 1, wherein said reagent providing step provides a reagent that includes a scintillation material.

5. The method of claim 1, wherein said reagent providing step provides a reagent that changes the pH or salt concentration in the capillary.

6. An apparatus for electrophoretic separation comprising:
   a first capillary;
   a device for providing a sample to the capillary;
   a device for providing to the capillary at a first location along the capillary a reagent that will react chemically in the capillary with the sample to aid in the detection or separation of the sample, said sample having components, thereby rendering at least a component of the sample detectable or enhancing the separation of the sample;
   a power supply for applying an electrical potential across the capillary, causing the sample to migrate through the capillary and to separate the sample in the capillary into its components; and
   a detector located at a second location along the capillary downstream from said first location for detecting at least one of said components of the sample.

7. The apparatus of claim 6, said reagent providing device comprising:
   a second capillary connected to the first capillary at said first location so that when a sample is moving in the first capillary, a reagent moving in the second capillary will mix with the sample in the first capillary, and
   a unit for providing the reagent through said second capillary tube to the first capillary.

8. The apparatus of claim 6, wherein said reagent includes a scintillation material.

9. The apparatus of claim 6, wherein said reagent changes the pH or salt concentration in the capillary.

* * * * *